United States Patent [19]

Euvrard

[11] Patent Number: 5,133,661
[45] Date of Patent: Jul. 28, 1992

[54] DENTISTRY HANDPIECE ABLE TO RECEIVE ONE OF A NUMBER OF VIBRATING INSTRUMENTS

[75] Inventor: Hubert Euvrard, Auxon-Dessus, France

[73] Assignee: Micro Mega S.A., Besancon, France

[21] Appl. No.: 529,187

[22] Filed: May 25, 1990

[30] Foreign Application Priority Data

May 26, 1989 [FR] France .................. 89 07137

[51] Int. Cl.⁵ .................................... A61C 3/03
[52] U.S. Cl. .................................... 433/120; 433/118; 433/87
[58] Field of Search .................. 433/118, 80, 127, 119, 433/120, 82, 87, 88

[56] References Cited

U.S. PATENT DOCUMENTS

| | | | |
|---|---|---|---|
| 3,081,980 | 3/1963 | Karlstrom et al. | 433/118 |
| 3,444,622 | 5/1969 | Mills et al. | 433/120 |
| 4,283,174 | 8/1981 | Sertich | 433/119 |
| 4,330,282 | 5/1982 | Nash | 433/118 |
| 4,353,696 | 10/1982 | Bridges | 433/119 |
| 4,484,891 | 11/1984 | Nash | 433/118 |
| 4,484,893 | 11/1984 | Finn | 433/118 |
| 4,575,338 | 3/1986 | Maizenberg | 433/126 |
| 4,578,033 | 3/1986 | Mossle et al. | 433/118 |
| 4,589,847 | 5/1986 | Loge et al. | 433/118 |
| 4,668,190 | 5/1987 | Overmyer | 433/80 |
| 4,781,589 | 11/1988 | Bareth | 433/127 |
| 4,874,314 | 10/1989 | Fleer et al. | 433/127 |
| 4,940,410 | 7/1990 | Apap et al. | 433/127 |

FOREIGN PATENT DOCUMENTS

| | | | |
|---|---|---|---|
| 0015672 | 9/1980 | European Pat. Off. | 433/118 |
| 0092861 | 11/1983 | European Pat. Off. | 433/118 |
| 2588182 | 4/1987 | France | 433/88 |

Primary Examiner—Robert P. Swiatek
Attorney, Agent, or Firm—Weiser & Stapler

[57] ABSTRACT

A dental handpiece which can receive one of a number of vibrating instruments for applications in endodontics or periodontal treatment includes an elongate handpiece for defining a body enclosing a non-rotating axle excited mechanically in vibration, mounted in the body by semi-flexible supports which contribute to generating and localizing a vibration node towards the front of the handpiece and to retain the vibrating axle centrally with its housing. A flexible interconnection is provided between the axle and the rotating driven shaft of the operating motor, to develop the vibrations which are desired.

18 Claims, 4 Drawing Sheets

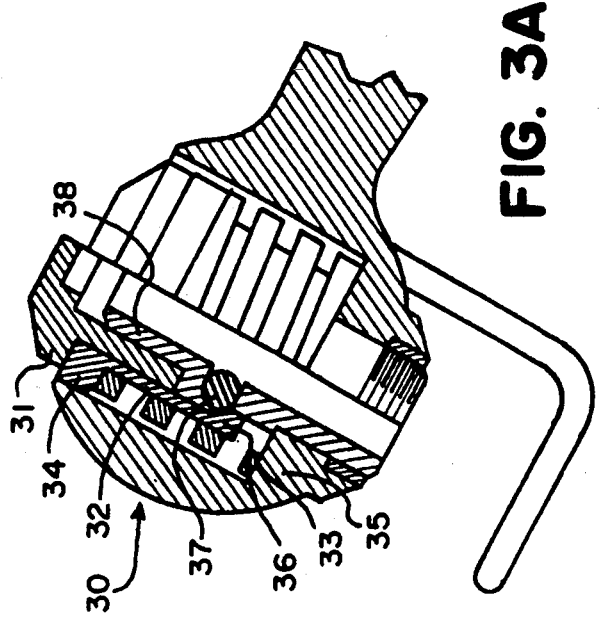
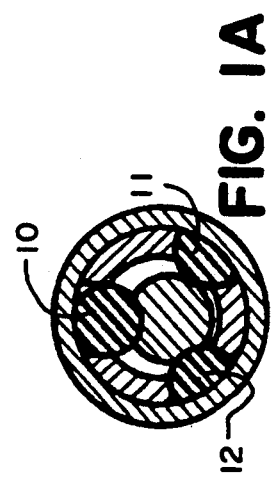
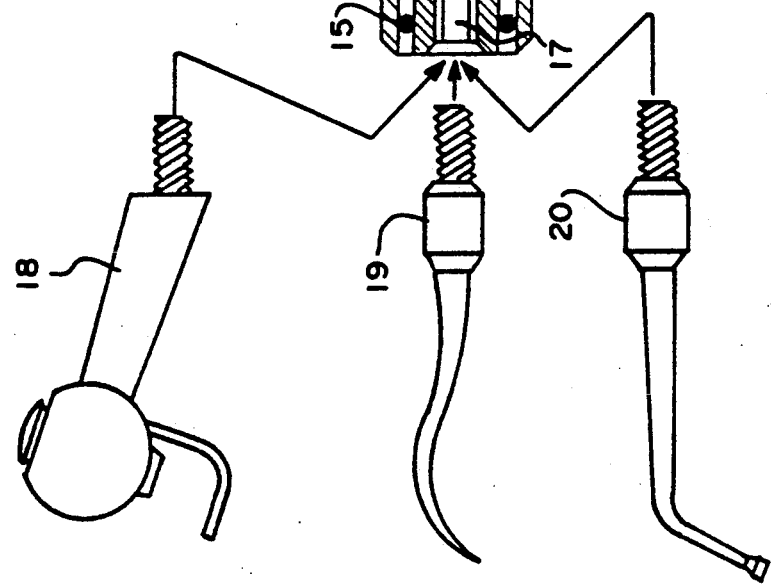
FIG. 3A
FIG. 1A
FIG. 1

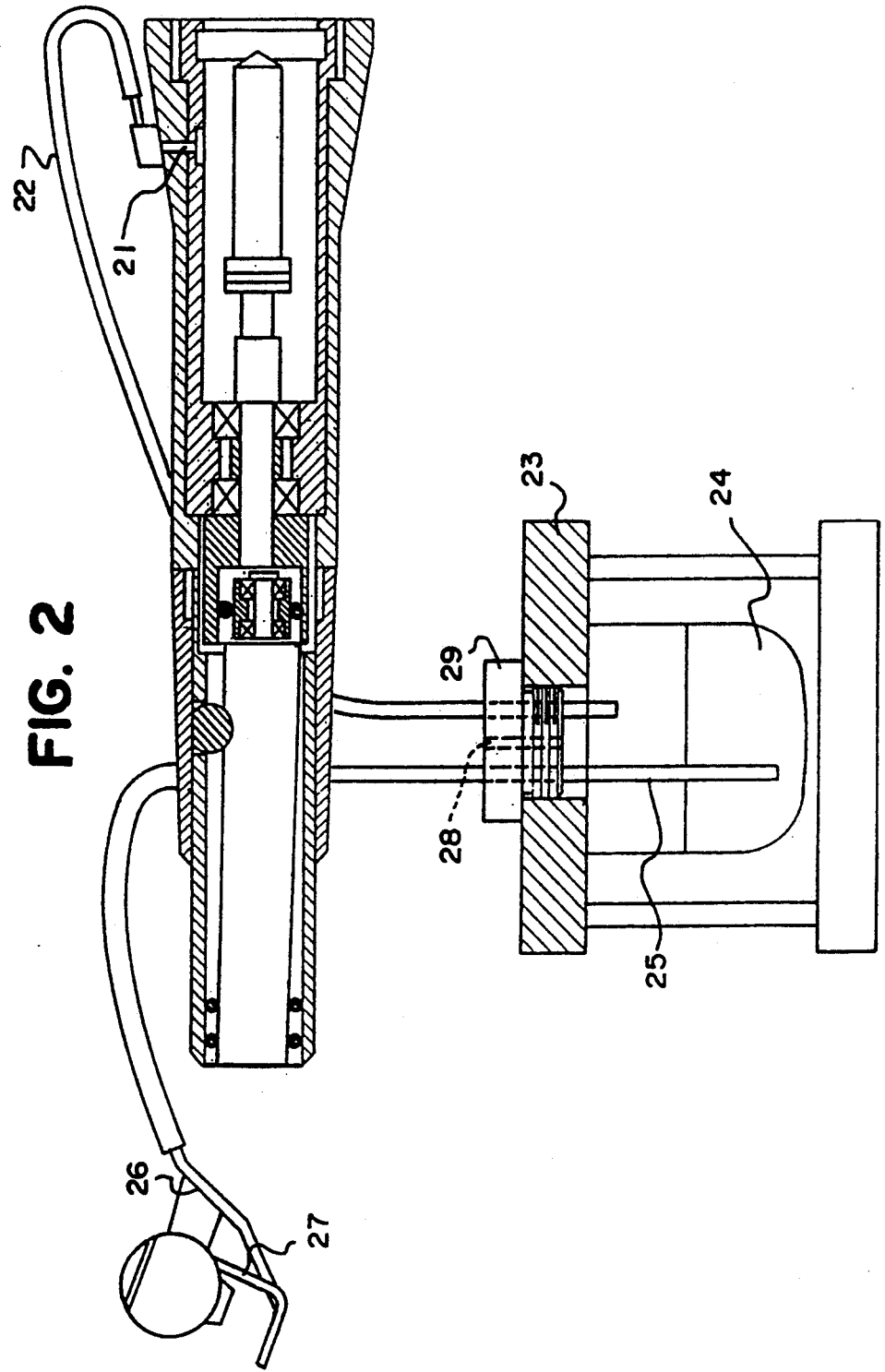

DENTISTRY HANDPIECE ABLE TO RECEIVE ONE OF A NUMBER OF VIBRATING INSTRUMENTS

The present invention relates to a dentistry handpiece able to receive one of a number of vibrating periodontal treatment.

Handpieces of this type are already known, but they all have a certain number of disadvantages.

Thus, apparatuses of the ultrasonic type are known, some of which permit the two abovementioned applications. The major disadvantage of these apparatuses is that of requiring specific control equipment for the generation of the ultrasonics.

Apparatuses are also known in which the vibration is generated by a device functioning on compressed air such as, for example, that described in Patent FR 2,505,172 in the name of the Applicant, which apparatuses do not necessitate specific equipment since they use the compressed air generally available on dental units, but their setting-up requires that the connection system be compatible with that which has been chosen by the manufacturer of the unit, and this is not straightforward because there are a large number of connection systems.

Finally, certain vibrating systems such as those described in application EP 0,305,357 and application EP 0,293,654 resolve the above problems but have the disadvantage of functioning:

either with endodontics instruments, or with instruments of the periodontal curette type.

Moreover, they have heads whose sizes are too large.

The aim of the present invention is to overcome these disadvantages of the dental handpieces of the prior art and to provide a handpiece which can receive both channel instruments for endodontic treatment and instruments of the scaling curette type, and even instruments for the cleaning of the subgingival spaces or else the vibration of amalgam, this in a non-limiting manner.

According to the invention, this result is achieved with a dentistry handpiece able to receive one of a number of vibrating instruments for applications in endodontics or periodontal treatment, characterized in that the said handpiece, of elongate form, essentially comprises a body of one or more front parts consisting of a non-rotating axle excited mechanically in vibration, the said shaft being mounted in the body by semi-flexible means of which at least one contributes to generating and localizing a vibration node towards the front and the other makes it possible to hold the vibrating shaft in the centre of its housing. This second means is advantageously made up of balls of rubbery material holding the shaft in the manner of a tripod, thereby leaving it mechanically free so as not to interfere with the vibration, while at the same time creating the vibration node.

The said flexible means will be essentially one or more O-ring seals.

According to an important characteristic of the invention, it is thus possible to produce a dental handpiece which is actuated by an air motor or electric motor universally used on the dental units corresponding to ISO Standard 3964.

The device for vibrational excitation is advantageously made up of an element mounted freely in rotation on the vibrating axle and coaxial relative to the latter, but offset relative to a drive element in communication with the input shaft of the handpiece of known type, the communication between the drive element and the rotary element of the vibrating axle being a flexible communication.

At its distal end the vibrating axle receives a head which can hold an endodontics instrument or a curette for example.

The handpiece according to the invention may optionally comprise a simple irrigation device if it is mounted on a motor provided with a spray air passage.

The invention will be better understood with the aid of the description which is given below with reference to the attached drawings, in which:

FIG. 1 is a longitudinal cutaway view of a handpiece according to the invention;

FIG. 1A is a section along A—A in FIG. 1;

FIG. 2 is a variant with an irrigation device;

FIG. 3A is a cutaway view of a specific head which can be mounted on the handpiece according to the invention;

FIG. 3B is a view of a tool handle designed to be used with the head in FIG. 3A;

Figure 4:
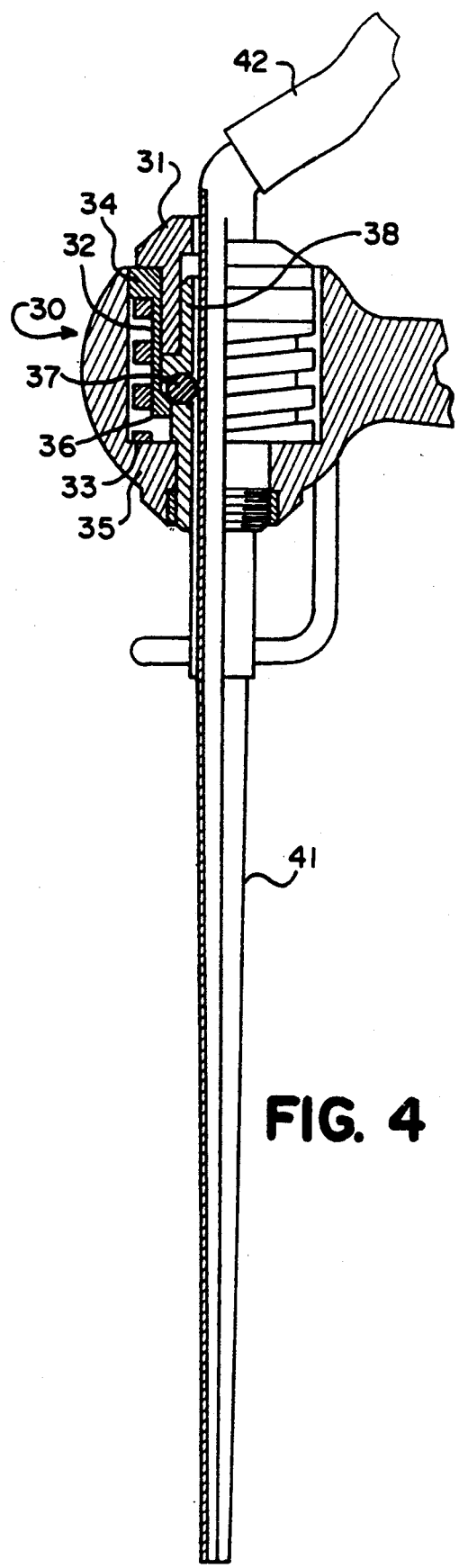
FIG. 4 is a longitudinal cutaway view of a specific head which can be used in endodontics.

The handpiece according to the invention, generally referred to by (1), usually comprises an oblong body (2) of one or more parts, enclosing a rotating shaft (3) driven in a manner known per se.

In the structure of the invention, this shaft comprises at its distal end a cylindrical cage (4) of longitudinal cross-section asymmetrical relative to the longitudinal axis of the shaft.

The cage (4) encloses a bearing (5) mounted floating inside the said cage (4) and connected to the latter by a flexible communication (6), for example an O-ring seal.

The bearing (5) is passed through by a longitudinal seat (7), offset axially relative to the axis of the shaft (3), of a driven shaft (8) which will be described hereinbelow.

It will be understood that the rotation of the shaft (3), through the bearing (9), drives the cage (4) in rotation. The latter in turn drives the bearing (5) by way of the flexible communication (6), and the bearing (5) stresses the seat and the driven shaft (8) with which the seat is integral.

The movement which results from this is an oscillating movement.

In order to focus a vibration node at the active end of the piece, the driven shaft (8) is stressed over its length by balls (10, 11, 12), or spherical caps, which are housed between the head sleeve (13) and the body sleeve (14) in corresponding housings in the head sleeve. These balls cooperate with corresponding recesses in the shaft (8) represented in FIG. 1A.

At its distal end, the shaft (8) is guided and cushioned at the level of the head sleeve (13) by one or two O-ring seals (15, 16). It comprises a receiver housing (17), threaded internally, intended to receive the instruments such as the head (18) or curettes (19, 20).

It will be understood that the combined action of the rotation of the cage stressing the axially offset seat (7)

and the bearings (10, 11, 12) form a structure with bearing point and tripod which results, at the distal end of the shaft (8), in the creation of a vibration node whose energy and amplitude are transmitted to the end of the tool or of the curette which is arranged thereon.

The absence of a piece with rotational movement confers upon the assembly of the head a simple and therefore reliable mechanical structure.

If the head (18) is used, it will be envisaged that the vibrating axle (8) and the drive axle (3) will be pierced along their whole length. A similar piercing is then made in the neck of the head (18) which leads into the tightening mechanism. The inside of the head is thus under pressure by virtue of the cooling air from the motor, which prevents the penetration of particles into the head.

In the variant in FIG. 2, a simple irrigation device has been provided

When the apparatus is mounted on a motor provided with a spray air passage, the pressurized spray air leaves the handpiece via a bore (21) and is conveyed via a tube (22) towards a receptacle (23) containing the irrigation liquid (24) which is thus pressurized, a tube (25) immersed in the liquid making it possible, under the effect of the pressure as soon as the apparatus is connected, to convey the liquid to the irrigation tube (26) situated on the neck (27) of the head body.

A hole (28) in the stopper (29) of the receptacle permits air pressure reduction when the instrument is stopped, thereby preventing the distribution of liquid from continuing.

The endodontics head can be of any type, for example with a push-button for the positioning or dismounting of the instrument, with a ball lock system which makes it possible, by virtue of striations made in the handle of the instrument, to control the position of the latter relative to the stop with which the said head is provided.

Thus, with reference to FIG. 3A, the head (30) comprises a push-button (31) which comes into direct engagement with a bushing (32). The bushing (32) is subjected to the return action of a helical spring (33) which bears on the one hand on a shoulder (34) of the head and on the other hand on the head body (35). The bushing (32) additionally comprises an annular shoulder (36) directed towards the inside of the head body and serving as a seat for one or more balls (37).

In the locking position of the head of the tool in the head body, by way of a bushing (38) screwed into the said head body, the ball (37) is in abutment against the shoulder (36).

If the push-button (31) is pressed, this movement displaces the shoulder (36) downwards relative to the head and releases the ball, and this unlocks the handle of the tool.

The handle (39) represented in FIG. 3B comprises a plurality of radial grooves (40) cooperating with the said balls.

The grooves make it possible to effect the adjustment of the working length of the tool.

They will preferably have an angle of opening of the order of 100°.

Figure 5:
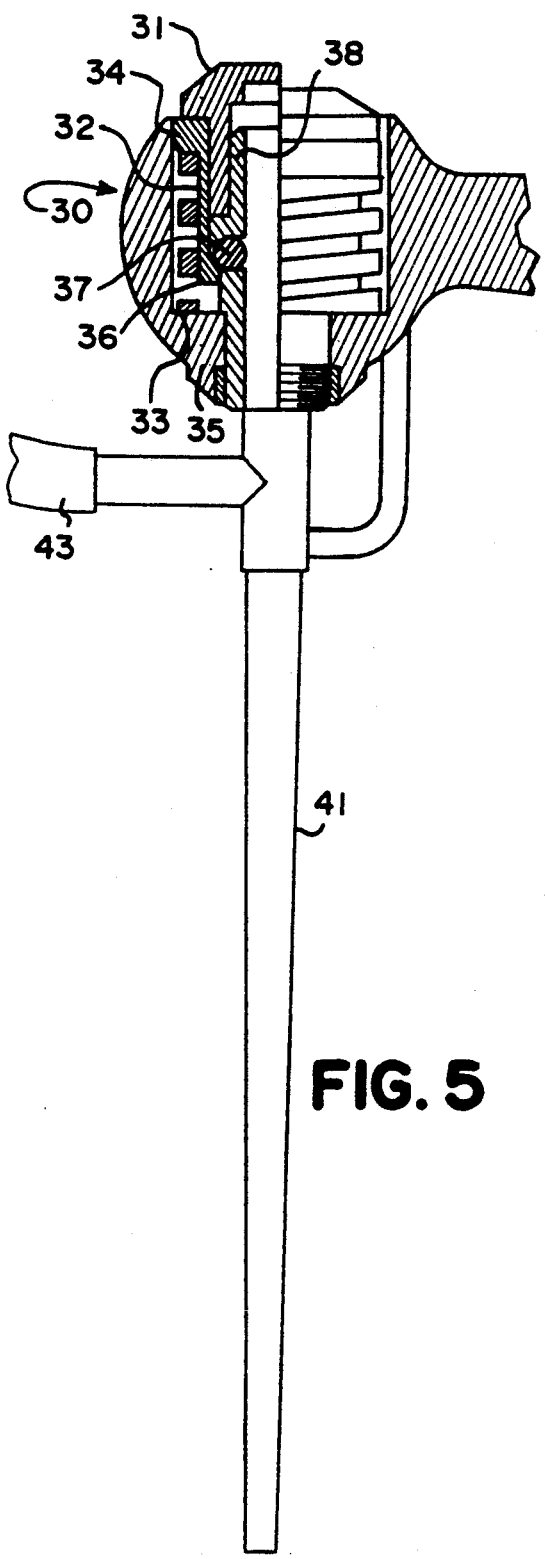
FIG. 5 is a longitudinal cutaway view of another specific head which can be used in endodontics.

Reference will now be made to FIGS. 4 and 5.

In endodontic operations, one of the principal problems is that of clearing the canal of all the dentine residues, which is particularly difficult at the apical level since, on the one hand, the irrigation medium used in the course of treatment cannot descend to this level because of the very presence of the instrument and, on the other hand, if an irrigation medium is conveyed into the canal after treatment, the turbulence at the apical level is insufficient to make the dentine debris rise.

The apparatus according to the invention is used to inject an irrigation medium (liquid) as far as the apex and to provoke, by means of the vibrations of the instrument, a level of turbulence which is sufficient for the dentine debris to rise and escape. For this purpose a hollow instrument (41) of low external diameter is used which permits injection of the liquid under pressure as far as the apex, which liquid is set in turbulent motion by means of the vibrations of the instrument.

The injection of liquid under pressure can be carried out above the head via a tube (42) or under the head via a tube (43).

The channel instrument (41) may, in order to promote the flow, be provided at its tip with one or two bevels.

Figure 6:
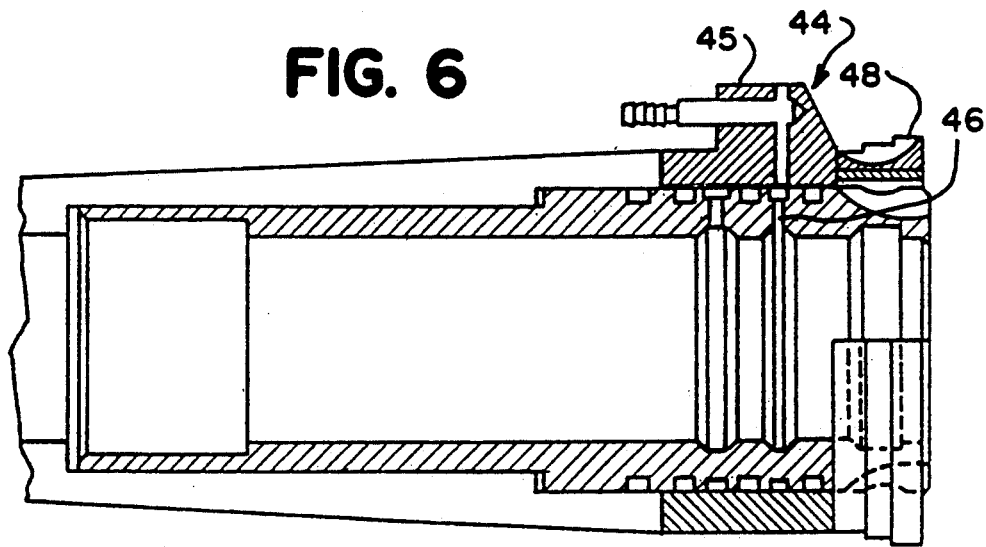
FIG. 6 is a longitudinal cutaway view of a handpiece provided with a device for supplying liquid towards the head of the contra-angle.
Figure 7:
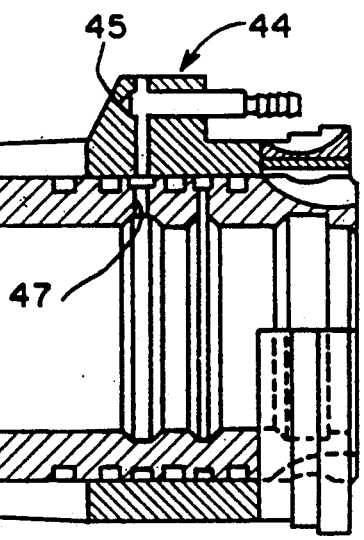
FIG. 7 is a longitudinal cutaway view of a handpiece provided with a device for supplying air under pressure.

In FIGS. 6 and 7 a handpiece is shown with an inversion device (44) making it possible to convey a fluid towards the head of the handpiece.

In the representation in FIG. 6, a socket (45) makes it possible to convey the liquid leaving the motor and arriving at a channel (46) directly towards the head of the contra-angle in order to be used there.

In the representation in FIG. 7, the socket (45) makes it possible to convey the air pressure leaving the motor and arriving at a channel (47) to a pneumatic control system for spraying, for example in accordance with Patent Application 89-155951 in the name of the Applicant.

In order to permit this inversion of direction, a ring (48) is mounted removably by snapping onto the body of the handpiece. By means of this procedure, the practitioner can choose the spraying mode:

either with water leaving the motor or with a device for distribution of physiological serum, for example.

I claim:

1. A dentistry handpiece for receiving a vibrating instrument for applications in endodontics and periodontal treatment, comprising an elongate handpiece defining a body for enclosing a non-rotating axle and means for exciting and mechanically vibrating the axle, wherein the exciting means includes a flexible interconnection between the axle and a rotating driven shaft in communication with the axle, and wherein the axle is mounted within the body by semi-flexible means for generating and localizing a vibration node toward distal portions of the axle and for retaining the axle centrally within the body.

2. The handpiece of claim 1 wherein the semi-flexible means are balls of elastomeric material oriented in a tripod arrangement which leaves the shaft mechanically free so as not to interfere with vibration, while simultaneously creating the vibration node.

3. The handpiece of claim 1 wherein the semi-flexible means includes at least one O-ring seal.

4. The handpiece of claim 1 wherein the driven shaft is rotated by an electric or air motor for dental units corresponding to ISO standard 3964.

5. The handpiece of claim 1 wherein the exciting means includes an element mounted freely in rotation on the axle, and coaxial relative to the axle, but offset relative to the driven shaft.

6. The handpiece of claim 5 wherein the driven shaft includes at a distal end a cylindrical cage of longitudinal cross-section which is asymmetrical relative to a longitudinal axis defined by the driven shaft, wherein the axle includes a bearing enclosed by the cage and mounted to float inside the cage, and wherein the flexible interconnection includes a bearing which passes through a longitudinal seat which is axially offset relative tot eh axis of the driven shaft.

7. The handpiece of claim 1 wherein the axle receives, at a distal end, a head for receiving an endodontics instrument or a curette.

8. The handpiece of claim 1 which further comprises a head including a push-button for direct engagement with a bushing subject to a return action responsive to a helical spring which bears at one end on a shoulder of the head and at another end on a portion of the head body.

9. The handpiece of claim 8 wherein the bushing further comprises an annular shoulder facing inner portions of the head body for seating at least one ball, and wherein the ball is held in abutment against the annular shoulder in a locking position of the head over the instrument in the head body by a bushing screwed into the head body.

10. The handpiece of claim 1 having a head for receiving an instrument with a handle comprised of a plurality of radial grooves.

11. The handpiece of claim 10 wherein the grooves define an opening angle of about 100°.

12. The handpiece of claim 1 wherein the handpiece is associated with a motor provided with a spray air passage, wherein the spray air is pressurized, and which further comprises a bore for delivering the spray air to a first tube and toward a receptacle containing an irrigation liquid, which is thereby pressurized, a second tube immersed in the pressurized liquid for conveying the liquid to a neck in the head body, and means for permitting a reduction in air pressure when operation of the instrument is stopped, thereby preventing further distribution of the liquid.

13. The handpiece of claim 1 having a head for receiving a curette.

14. The handpiece of claim 13 wherein the axle and the driven shaft are pierced along their length, and wherein the head has a neck which leads into a tightening mechanism and which is also pierced.

15. The handpiece of claim 14 which further comprises a channel instrument supplied with a pressurized liquid through a communicating tube.

16. The handpiece of claim 15 wherein the channel instrument has a tip provided with at least one bevel.

17. The handpiece of claim 1 wherein the shaft is driven by a motor, and which further comprises a socket for conveying liquid from the motor to a channel directed toward the head of the handpiece.

18. The handpiece of claim 1 wherein the shaft is driven by a motor, and which further comprises a socket for developing an air pressure leaving the motor and arriving at a channel, wherein the socket is removably mounted by snap-fit engagement with the body of the handpiece for inverting the direction of the socket.

* * * * *